United States Patent [19]

Robinson et al.

[11] Patent Number: 4,564,603

[45] Date of Patent: * Jan. 14, 1986

[54] OXIDATIVE-DEHYDROGENATION CATALYST AND PROCESS

[75] Inventors: Paul R. Robinson; Eric L. Moorehead, both of Diamond Bar, Calif.

[73] Assignee: Union Oil Company of California, Los Angeles, Calif.

[*] Notice: The portion of the term of this patent subsequent to Jun. 12, 2001 has been disclaimed.

[21] Appl. No.: 667,000

[22] Filed: Oct. 31, 1984

Related U.S. Application Data

[60] Continuation-in-part of Ser. No. 592,422, Mar. 21, 1984, which is a division of Ser. No. 328,446, Dec. 7, 1981, Pat. No. 4,454,245, which is a continuation-in-part of Ser. No. 595,333, Mar. 30, 1984, which is a division of Ser. No. 335,531, Dec. 29, 1981, Pat. No. 4,455,388, which is a continuation-in-part of Ser. No. 328,446, Dec. 7, 1981, Pat. No. 4,454,245, which is a continuation-in-part of Ser. No. 461,942, Jan. 28, 1983, Pat. No. 4,481,363, which is a division of Ser. No. 289,806, Aug. 3, 1981, Pat. No. 4,388,221, which is a continuation-in-part of Ser. No. 646,291, Aug. 29, 1984, which is a continuation-in-part of Ser. No. 461,942, , which is a continuation-in-part of Ser. No. 492,163, May 6, 1983, which is a continuation-in-part of Ser. No. 492,226, May 6 1983, each is a continuation-in-part of Ser. No. 275,.70, Jun. 19, 1981, abandoned.

[51] Int. Cl.$^4$ .................. B01J 29/06; B01J 21/08; B01J 27/00

[52] U.S. Cl. .................. 502/60; 502/64; 502/78; 502/209; 502/214

[58] Field of Search .................. 502/60, 64, 71, 209, 502/214, 78

[56] References Cited

U.S. PATENT DOCUMENTS

| | | | |
|---|---|---|---|
| 3,156,705 | 11/1964 | Kerr | 260/346.8 |
| 3,243,385 | 3/1966 | Sennewald et al. | 252/437 |
| 3,288,721 | 11/1966 | Kerr | 502/209 |
| 3,370,081 | 2/1968 | Sennewald et al. | 502/209 X |
| 3,506,400 | 4/1970 | Eberly, Jr. et al. | 23/182 |
| 3,640,681 | 2/1972 | Pickert | 252/455 |
| 3,700,749 | 10/1972 | Robinson et al. | 260/683.3 |
| 3,702,886 | 11/1972 | Argauer et al. | 423/328 |
| 3,751,502 | 8/1973 | Hayes et al. | 502/78 X |
| 3,775,508 | 11/1973 | Pitzer | 260/680 E |
| 3,789,078 | 1/1974 | Nolan et al. | 260/680 E |
| 3,856,881 | 12/1974 | Manning | 260/680 E |
| 3,862,146 | 1/1975 | Boghosian | 260/346.8 A |
| 3,867,411 | 2/1975 | Raffelson et al. | 260/346.8 A |
| 3,884,835 | 5/1975 | Vaughan | 252/451 |
| 3,888,886 | 6/1975 | Young et al. | 260/346.8 |
| 3,890,218 | 6/1975 | Morrison | 502/78 X |
| 3,914,332 | 10/1975 | Dickason | 260/680 E |
| 3,915,892 | 10/1975 | Harrison | 252/435 |
| 3,925,447 | 12/1975 | Gelbein | 260/465 C |
| 3,927,138 | 12/1975 | Walker | 260/680 E |
| 3,931,046 | 1/1976 | Weinstein et al. | 252/429 R |
| 3,972,832 | 8/1976 | Butter et al. | 502/78 X |
| 3,977,998 | 8/1976 | Freerks et al. | 252/435 |
| 4,061,724 | 12/1977 | Grose et al. | 423/335 |
| 4,062,873 | 12/1977 | Harrison | 260/346.75 |
| 4,064,070 | 12/1977 | Harrison | 252/435 |
| 4,073,865 | 1/1978 | Flanigen et al. | 423/339 |
| 4,092,269 | 5/1978 | Mount et al. | 252/435 |
| 4,104,294 | 8/1978 | Grose et al. | 260/448 |
| 4,123,388 | 10/1978 | Kerr et al. | 252/437 |
| 4,151,116 | 4/1979 | McDermott | 252/435 |
| 4,153,577 | 5/1979 | Barone | 252/435 |
| 4,165,299 | 8/1979 | Pederson | 252/435 |
| 4,165,300 | 8/1979 | Dolhyj et al. | 252/462 |
| 4,171,316 | 10/1979 | Pederson | 260/346.75 |
| 4,179,404 | 12/1979 | Barone | 252/435 |
| 4,206,084 | 6/1980 | Strojny | 252/455 R |
| 4,244,879 | 1/1981 | Bremer | 260/346.75 |
| 4,246,141 | 1/1981 | Hass et al. | 252/455 Z |
| 4,246,421 | 1/1981 | Bartek et al. | 546/352 |

(List continued on next page.)

FOREIGN PATENT DOCUMENTS 0035807 9/1981 European Pat. Off.

OTHER PUBLICATIONS

"When is a Zeolite Not a Zeolite?", by Lovat V. C. Rees, Nature, vol. 296, pp. 491-492, Apr. 8, 1982.

"Silicalite-2, A Silica Analogue of the Aluminosilicate Zeolite ZSM-11", by D. M. Bibby et al., Nature, vol. 280, pp. 664-665, Aug. 23, 1979.

"Silicalite, A New Hydrophobic Crystalline Silica Molecular Sieve", by E. M. Flanigen et al., Nature, vol. 271, pp. 512-516, Feb. 9, 1978.

"Chemical and Physical Properties of the ZSM-5 Substitutional Series", by D. H. Olson et al., Journal of Catalysis, vol. 61, pp. 390-396, (1980).

"Silicates", by Cotton and Wilkinson, Advanced Inorganic, 2nd ed., 1966, pp. 469-474.

"The Structure and the Activity of Vanadyl Phosphate Catalysts", by Michihiro Nakamura et al., Journal of Catalysis, vol. 34, pp. 345-355, (1974).

"Reactions on ZSM-5-Type Zeolite Catalysts", by J. R. Anderson et al., Journal of Catalysis, vol. 58, pp. 114-130, (1979).

"Pentasil Family of High Silica Crystalline Materials", (List continued on next page.)

Primary Examiner—Carl F. Dees
Attorney, Agent, or Firm—Gregory F. Wirzbicki; Dean Sandford

[57] ABSTRACT

Oxidative dehydrogenation catalysts suitable for converting $C_4$ to $C_8$ mono-olefins to conjugated dienes comprise vanadium, phosphorus, and alkali metal components, and preferably also a tin component, in combination with a microporous crystalline silica or a crystalline zeolite having a silica-to-alumina ratio of at least 6.0. In one embodiment, the catalyst has a surface area between 30 $M^2/g$ to 450 $M^2/g$ and the vanadium has an average valence in the range of from 3.50 to 4.95.

17 Claims, No Drawings

U.S. PATENT DOCUMENTS

| | | | |
|---|---|---|---|
| 4,247,419 | 1/1981 | Vartuli et al. | 252/435 |
| 4,252,680 | 2/1981 | Walker et al. | 252/435 |
| 4,270,017 | 5/1981 | Young | 585/437 |
| 4,283,306 | 8/1981 | Herkes | 252/432 |
| 4,292,201 | 9/1981 | Vartuli et al. | 252/435 |
| 4,292,202 | 9/1981 | Vartuli et al. | 252/435 |
| 4,309,275 | 1/1982 | Mulasky | 208/109 |
| 4,309,276 | 1/1982 | Miller | 208/109 |
| 4,311,611 | 1/1982 | Sasaki et al. | 252/412 |
| 4,314,983 | 2/1982 | Hass et al. | 423/542 |
| 4,333,853 | 6/1982 | Milberger et al. | 252/435 |
| 4,347,395 | 8/1982 | Chu et al. | 585/420 |
| 4,360,453 | 11/1982 | Lemanski et al. | 252/435 |
| 4,361,501 | 11/1982 | Blum et al. | 252/435 |
| 4,362,653 | 12/1982 | Robinson | 252/455 R |
| 4,370,490 | 1/1983 | Gruber et al. | 560/214 |
| 4,388,221 | 6/1983 | Moorehead | 252/435 |
| 4,396,536 | 8/1983 | Bremer et al. | 252/437 |
| 4,428,862 | 1/1984 | Ward et al. | 502/77 |
| 4,454,245 | 6/1984 | Robinson et al. | 502/209 |
| 4,454,342 | 6/1984 | Gaffney et al. | 560/204 |
| 4,455,388 | 6/1984 | Robinson et al. | 502/209 |
| 4,481,363 | 11/1984 | Moorehead | 549/260 |

OTHER PUBLICATIONS by C. T. Kokotailo et al., in *The Properties and Applications of Zeolites*, ed. R. P. Townsend, the Proceedings of a Conference organized jointly by the Inorganic Chemical Group of the Chemical Society and The Society of Chemical Industry, (Burlington House, London), Apr. 18–20, 1979, pp. 134–139.

"Resolving Crystallographically Distinct Tetrahedral Sites in Silicalite and ZSM-5 by Solid-State NMR", by C. A. Fyfe et al., *Nature*, vol. 296, Apr. 8, 1982, pp. 530–533.

"Research Article Triggers Dispute on Zeolite" by Budiansky, *Nature*, vol. 300, Nov. 1982, p. 309.

"Zoned Aluminium Distribution in Synthetic Zeolite ZSM-5" by Ballmoos et al., *Nature*, vol. 289, Feb. 26, 1981, pp. 782–783.

OXIDATIVE-DEHYDROGENATION CATALYST AND PROCESS

CROSS-REFERENCE TO RELATED APPLICATIONS

This application is a continuation-in-part of U.S. patent application Ser. No. 592,422 filed Mar. 21, 1984, which itself is a division of U.S. patent application Ser. No. 328,446 filed Dec. 7, 1981, now U.S. Pat. No. 4,454,245, and this application is also a continuation-in-part of U.S. patent application Ser. No. 595,333 filed Mar. 30, 1984, which itself is a divisional of U.S. patent application Ser. No. 335,531, filed Dec. 29, 1981, now U.S. Pat. No. 4,455,388, which is a continuation-in-part of U.S. patent application Ser. No. 328,446 filed Dec. 7, 1981, now U.S. Pat. No. 4,454,245 which is a continuation-in-part of U.S. patent application Ser. No. 461,942 filed Jan. 28, 1983, now U.S. Pat. No. 4,481,363, which is itself a divisional of U.S. patent application Ser. No. 289,806 filed Aug. 3, 1981, now U.S. Pat. No. 4,388,221, and this application is also a continuation-in-part of U.S. patent application Ser. No. 646,291, filed Aug. 29, 1984, which itself is a continuation-in-part of the aforesaid application Ser. No. 461,942, now U.S. Pat. No. 4,481,363, which is a divisional application of the aforesaid Ser. No. 289,806, now U.S. Pat. No. 4,388,221, and this application is also a continuation-in-part of U.S. patent application Ser. No. 492,163, filed May 6, 1983, and a continuation-in-part of U.S. patent application Ser. No. 492,226, filed May 6, 1983, both of which applications are continuation-in-part applications of U.S. patent application Ser. No. 275,370, filed June 19, 1981, abandoned.

BACKGROUND OF THE INVENTION

The present invention relates to oxidative dehydrogenation catalysts, and more particularly to oxidative dehydrogenation catalysts useful for producing diolefins from $C_4$ to $C_8$ mono-olefins.

The use of dehydrogenation catalysts to oxidize hydrocarbons to diolefins is known and appreciated by the prior art. For example, U.S. Pat. No. 3,927,138 relates to a process for producing diolefins from paraffins, especially the dehydrogenation of butane to butenes and butadiene, using an oxidation catalyst comprising a ferrous metal, tin, phosphorus and an alkali metal. The catalysts may be supported on or diluted with materials such as silica, alumina, boria, etc.

U.S. Pat. No. 3,914,332 discloses a process for the oxidative dehydrogenation of butane to a mixture of butenes and butadiene using a vanadium-potassium-sulfur catalyst supported on silica, which permits the use of high space velocities.

U.S. Pat. No. 3,856,881 relates to a process for the dehydrogenation of $C_4$ to $C_5$ hydrocarbons to produce the corresponding dehydrogenated compounds. The dehydrogenation catalyst used contains a crystalline spinel of a phosphorus and divalent-metallic vanadium compound. Catalyst carriers such as alumina, pumice, silicon, etc., are additionally described as suitable for use in the dehydrogenation catalyst.

U.S. Pat. No. 3,789,078 discloses a dehydrogenation process and dehydrogenation catalysts useful for oxidatively dehydrogenating organic compounds such as alkenes, alkadienes, cycloalkenes, alkylpyridines and alkyl aromatics. The catalyst contains a combination of phosphorus, tin, and a Group IA or IIA metal of the Periodic Table. Substantially any phosphorus, tin, and Group IA or IIA-containing materials may be employed in the catalyst so long as at least one of the materials used contains oxygen.

U.S. Pat. No. 3,775,508 relates to an oxidative dehydrogenation process for dehydrogenating $C_2$ to $C_{10}$ alkenes, alkadienes, etc., using an oxidation catalyst containing phosphorus, tin, and a group IA or IIA metal of the Periodic Table. The catalyst is improved by including a heat-volatile activity-stimulating ammonium salt in the catalyst composition prior to the catalyst particle-forming stage.

As a rule, the prior art has avoided the use of crystalline aluminosilicate zeolites as support materials in catalysts for the oxidative dehydrogenation of hydrocarbons. Crystalline aluminosilicate zeolites are known to be useful in many hydrocarbon conversion reactions, such as cracking, hydrocracking, etc. But for hydrocarbon oxidation reactions and oxidative dehydrogenation reactions, the art has not succeeded with zeolitic catalysts.

Accordingly, it is an object of the invention to provide catalysts, and particularly zeolitic catalysts, and methods for their preparation and use, which are useful for oxidative dehydrogenation reactions, especially the conversion of $C_4$ to $C_8$ mono-olefins to a conjugated diene.

It is yet a further object to provide a method for producing such catalysts containing vanadium in an average valence in the range of $+3.50$ to $+4.95$.

A further object of the present invention is to provide a method for obtaining improved yields and selectivity of conjugated dienes from the corresponding mono-olefin, e.g., butadiene from butene.

These and other objects are accomplished according to the present invention by oxidizing a $C_4$ to $C_8$ mono-olefin to the corresponding diolefin in the presence of an alkali metal-promoted oxidative dehydrogenation catalyst comprising the oxides of vanadium and phosphorus (and optionally and preferably, tin) on a support containing a microporous crystalline silica or a crystalline zeolite having a silica-to-alumina ratio of at least 6.0.

SUMMARY OF THE INVENTION

The present invention is founded on the discovery that catalysts containing vanadium, phosphorus and alkali metal components are useful in combination with carriers containing one or more crystalline zeolites for promoting oxidative dehydrogenation reactions, provided the zeolites have a silica-to-alumina ratio ($SiO_2$:$Al_2O_3$) of at least 6.0. The present invention, therefore, provides an oxidative dehydrogenation catalyst wherein tne catalyst comprises the elements and/or compounds of vanadium, phosphorus, and an alkali metal, and preferably also tin or a compound thereof, on a support material comprising a crystalline zeolite having a silica-to-alumina ratio of at least 6.0. The invention further provides a method for producing a conjugated diene from a mono-olefin by contacting a $C_4+$ mono-olefin with a gas containing molecular oxygen in the vapor phase, under reaction conditions, with a zeolitic catalyst of the invention.

In addition to zeolites of high silica-to-alumina content, it has also been discovered that crystalline silicas are useful in combination with vanadium and phosphorus, and optionally and preferably tin, for oxidative dehydrogenation reactions. Particularly useful crystalline silicas are those containing numerous micropores, such as silicalite.

The invention is founded on yet another discovery, namely, that vanadium-phosphorus catalysts are rendered particularly suitable for oxidative-dehydrogenation reactions, such as the conversion of mono-olefins to conjugated dienes, by the addition of one or more alkali metals thereto. Preferred among such catalysts are those which contain alkali metals in a ratio to phosphorus of at least 0.10 to 1. Also preferred in such catalysts is the presence of tin, particularly in a ratio to phosphorus of at least 0.001 to 1.0.

The invention additionally provides a method of preparing a vanadium, phosphorus, rin, alkali metal oxidation catalyst which comprises:

(A) forming a catalyst precursor by reacting a vanadium compound, a phosphorous compound, and an alkali metal compound in an acidic aqueous solution with a divalent tin compound under reaction conditions which will provide vanadium having an average oxidation state of +3.50 to +4.95;

(B) combining the catalyst precursor with a carrier material, preferably containing a zeolite having a SiO$_2$:Al$_2$O$_3$ of at least 6.0; and (C) calcining the resultant material at an elevated temperature.

DETAILED DESCRIPTION OF THE INVENTION

Catalysts of the present invention comprise the elements and/or compounds, but most preferably the oxides, of vanadium, phosphorus, and an alkali metal, and preferably tin, on a support material comprising a microporous crystalline silica or a microporous crystalline zeolite of silica-to-alumina ratio of at least 6.0, preferably at least 8.0, and most preferably at least 10.0. It is also preferred that the vanadium in the catalyst have an average valence between +4.10 and +4.70, although vanadium in other average valence states, for example, in the range of +3.50 to +4.95, is also useful. In a preferred embodiment, the catalyst contains vanadium, phosphorus, tin, and one or more alkali metals according to the following expression:

$$M_a V_b P_c Sn_d X_e$$

where M is the total alkali metals a is 0.10 to 2, b is from 0.10 to 1, c is 1, d is from 0.001 to 0.30, and X is one or more anionic species (usually and preferably oxygen) present in an amount which satisfies the valence requirements of the vanadium, phosphorus, tin, and alkali metals. It will be understood by those skilled in the art that the numbers assigned to the subscript letters a, b, c, d, and e represent the atomic ratio pertaining to the vanadium, phosphorus, tin, and alkali metal components while the value for e merely satisfies the valence requirements for the particular combination of vanadium, phosphorus, tin, and alkali metal chosen.

One disadvantage of using acidic catalysts to produce diolefins from mono-olefins is that basic products have a tendency to remain on the catalyst surface and react further. Thus, a reaction to produce diolefins from mono-olefins and alkanes would, under tnese circumstances, proceed to a more acid product, for example, maleic anhydride from butene or butane. This problem is solved by the addition of an alkali metal promoter to the acidic dehydrogenation catalyst to render said catalyst less acidic. Although the invention is not limited to any theory, it is believed that a basic product or molecule, for example, 1,3-butadiene when butene is the feed source, will desorb from said catalyst rather than remain on the catalyst surface to react further and produce an acidic product or compound. This concept may be further described by the fact tnat the energy required to remove an electron (the ionization potential) from a basic molecule is smaller than the energy similarly required from an acid molecule (at least when comparing molecules of similar size such as butane, butene, and butadiene). Selective oxidation reactions can therefore be classified into various types, depending on the ionization potential of the hydrocarbon reaction and of the hydrocarbon product. For example, the reaction of butene to butadiene may be classified as a basic-to-basic-type reaction, while the reaction of butadiene to maleic anhydride may oe classified as a basic-to-acidic-type reaction. For the basic-to-basic or mono-olefin-to-diolefin reaction to proceed, there must be cooperative action between both acidic and basic sites on the catalyst. For example, basic reactant molecules are dissociatively adsorbed on acidic sites which extract a hydrogen atom as H$^-$ and thus generate an allyl radical. The radical moves to a neighboring basic site where it loses a second hydrogen and is partially oxidized to the resulting basic product. The product, being basic, easily desorbs from the basic site. Oxygen near the basic site is replaced by an oxygen of the catalyst lattice which is near an acidic site, and the oxygen of the gaseous phase replenishes tne latter. Thus, good selectivities for reactions of the basic-to-basic type need both acidic and basic sites on the catalyst surface.

From another perspective, the addition of an alkali metal to a vanadium-phosphorus hydrocarbon oxidation catalyst is theorized to affect the redox potential between 4 and 5 of vanadium. Alkali metals decrease this potential, making the V-P catalyst less of an oxidation catalyst. Thus, the catalyst loses its activity for oxidizing hydrocarbons such as butane to maleic anhydride and, instead, becomes more selective for milder oxidation reactions, such as the conversion of butene to butadiene.

The catalyst of the present invention is most usually prepared by first preparing a catalyst precursor containing the promoters desired in the final catalyst, i.e., vanadium, phosphorus, alkali metal, and preferably tin.

Alkali metals which are suitable for the catalyst precursor herein include lithium, sodium, potassium, rubidium, and cesium. The preferred alkali metal is potassium. Suitable alkali metal compounds useful as a source of alkali metals are selected from alkali metal salts such as the phosphates, i.e., meta, ortho, pyro, tri, etc., the carbonates, chlorides, oxalates, and acetates. An especially desirable alkali metal compound is potassium meta phosphate.

The vanadium components useful as a source of vanadium for the catalyst precursor herein include vanadium itself and many of its compounds, such as ammonium metavanadate and vanadyl sulfate; vanadium oxides, such as vanadium pentoxide; and vanadium oxyhalides, such as vanadium oxytrichloride. Pentavalent vanadium compounds such as ammonium metavanadate and vanadium pentoxide are most highly preferred. However, vanadium in nitrate solutions should be avoided, since nitrates tend to oxidize the vanadium.

The phosphorus components useful as a source of phosphorus in the catalyst of the invention include phosphorus itself as well as the compounds thereof. Normally chosen, however, are phosphorus compounds selected from phosphoric acid, phosphorus pentoxide, ammonium phosphate and diammonium phosphate. The preferred phosphorus compounds are pentavalent phosphorus compounds such as phosphoric acid and phosphorus pentoxide.

It is also highly preferred that a reducing agent be present in the catalyst precursor employed to prepare the catalyst of the invention. It is even more preferable that the reducing agent be selected from reducing agents containing tin, and particularly from divalent tin compounds. Divalent tin compounds employed are preferably selected from stannous chloride, stannous fluoride, stannous bromide, stannous oxide, stannous sulfate, stannous acetate, stannous pyrophosphate, and stannous oxalate. Upon reaction of the tin compound with the vanadium compound, tin $+2$ (stannous) will be oxidized up to the tin $+4$ (stannic) oxidation state while vanadium in the $+5$ oxidation state will be reduced to an average oxidation state less than $+5$.

The catalyst precursor is preferably produced by dissolving and mixing compounds of an alkali metal, vanadium, phosphorus and tin in an alcohol-containing acidic-aqueous medium such as an ethanol-water mixture further containing hydrochloric acid, hydroiodic acid, hydroformic acid, acetic acid, oxalic acid, maleic acid, citric acid or formic acid. The alkali metals, vanadium, phosphorus, and tin compounds are preferably contacted in proportions such that that atomic ratio of alkali metals to phosphorus is between about 0.1 to 1 and 2 to 1; the atomic ratio of vanadium to phosphorus is between 0.1 to 1 and 1 to 1; and the atomic ratio of tin to phosphorus is between 0.001 to 1 and 0.3 to 1. Preferred ratios are such that the alkali metal-to-phosphorus ratio is between 0.4 to 1 and 1 to 1, the vanadium-to-phosphorus ratio is between 0.2 to 1 and 1 to 1, and the tin-to-phosphorus ratio is between 0.002 to 1 and 0.2 to 1. The atomic ratio of vanadium to phosphorus in the starting materials is important since it controls the vanadium to phosphorus atomic ratio in the final catalyst. When the catalysts herein contain a vanadium:-phosphorus atomic ratio below 0.10 or above 1.0, the yield of diolefin decreases so low as to render the reaction commercially unattractive. It should be noted that phosphorus aids in stabilizing vanadium in the final catalyst composition, the alkali metal renders the catalyst surface basic, thus favoring the conversion of mono-olefins to diolefins, and tin $+2$ acts as a reducing agent which aids in the reduction of vanadium to a valence state of less than $+5$. It should additionally be noted that the above-described acids which dissolve the alkali metal, vanadium, phosphorus and tin compounds induce a reaction reducing the vanadium compounds. However, the reduction process takes from one-half hour to about one hour when tin is not present in the reaction medium. Upon the addition of divalent tin to the reaction medium, the reduction of vanadium to a valence of less than $+5$ takes place almost instantly, i.e., less than one minute. Generally, the vanadium is reduced to an average valence within the range of from $+3.50$ to $+4.95$, preferably from $+4.10$ to $+4.70$. (The average oxidation state of vanadium is determined herein by the method described by Nakamura et al. in "The Structure and the Activity of Vanadyl Phosphate Catalysts," *Journal of Catalysis,* Volume 34, pages 345 to 355 (1974).)

To prepare the catalyst precursor, conditions are employed to dissolve and react the alkali metal, vanadium, tin, and phosphorus in an aqueous media. Temperatures of from 100° F. to 220° F., preferably from 180° F. to 220° F., coupled with a reaction time from ½ hour to 6 hours, normally are sufficient at atmospheric pressure to dissolve and react the alkali metal, vanadium, phosphorus and tin compounds. However, pressures up to 50 p.s.i.g. may be used to shorten the dissolution and reaction times. Generally, agitation effected by mixing, rocking, shaking, stirring etc., is supplied during the reaction period to ensure complete contact of the reactants.

After the reaction proceeds to completion, the catalyst precursor is concentrated, collected, and, if desired, converted into an unsupported catalyst by calcining. However, it will most usually be the case that the catalytic active components will be desired in the supported form, and thus, the concentrated catalyst precursor is typically admixed with a carrier material, such as activated carbon, or a porous inorganic refractory oxide, such as silica gel, alumina, silica-alumina, or other materials known to provide a relatively large surface area for catalytic reactions.

In the preferred embodiment of the invention, the carrier material contains a microporous crystalline silica or a crystalline zeolite. Particularly preferred are those crystalline silicas and crystalline zeolites which are useful as molecular sieves.

As defined herein, a zeolite is any microporous crystalline substance having cation exchange properties. The preferred zeolites are any of the known natural or synthetic crystalline aluminosilicates having a silica-to-alumina ratio of at least 6.0, preferably at least 8.0, and most preferably at least 10.0, with the kinetic diameter of the pores of the zeolite being at least 5.0 angstroms. The requirement of a silica-to-alumina ratio of at least 6.0 eliminates many well-known zeolites for use herein. For example, zeolite Y is known to vary in silica-to-alumina ratio from 3.0 to 6.0 and even higher. Thus, those forms of Y zeolite of silica-to-alumina ratio greater than 6.0 may be used in the invention, but since most of the common forms of Y zeolite have a silica-to-alumina ratio below 6.0, it can be seen that the requirement herein for a silica-to-alumina ratio of at least 6.0 excludes from the invention most of the Y zeolites presently employed on a commercial basis for cracking, hydrocracking, etc.

Among the many zeolites which may be used in the invention include LZ-210, LZ-211, LZ-10, and LZ-20, all of which are available from Union Carbide. (LZ-210 and LZ-211 are more fully described in European Patent Application Pub. No. 82,211 of Breck et al., herein incorporated by reference in its entirety.) Another useful zeolite is SAPO-5, and others contemplated are zeolites of silica-to-alumina ratio above 6.0 which have been fluorided, preferably by the method disclosed in U.S. Pat. No. 4,297,335, which is herein incorporated by reference in its entirety. Whatever zeolite is employed in the invention, the hydrogen form, imparting acidity to the zeolite, is preferred. Such hydrogen zeolites may be prepared by acid-treating the corresponding sodium zeolite with relatively strong mineral acids, for example hydrochloric acid, nitric acid, etc. Yet other methods for yielding hydrogen zeolites are known in the art.

The most preferred zeolite for use in this invention, i.e., mordenite, is a highly siliceous zeolite generally characterized by a silica-alumina mole ratio range of from about 6 to about 20 as found in nature. The mordenite crystal lattice comprises as the basic building block a tetrahedron consisting of one silicon or aluminum atom surrounded by four oxygen atoms. Each tetrahedron belongs to one or more four and five-membered rings in the framework. The high degree of thermal stability of mordenite is probably due to the large number of five-membered rings which are energetically favored in terms of stability.

Rings of twelve tetrahedra form pores or channels running parallel along the crystal axis of mordenite to give a tubular configuration. This structure is unique among the aluminosilicates or zeolites, because the channels or tubes do not intersect, and access to the cages or cavities is in one direction only. For this reason mordenite is referred to as two-dimensional. Other well known zeolites, for example, faujasite, etc., contain twelve membered rings of tetrahedra, but they have interconnected cages which allow access from three directions.

Commercially available mordenites range in silica-to-alumina ratio from about 6:1 to as high as 100:1, and even higher silica-to-alumina ratios are possible. Typical synthetic mordenites are prepared by heating an alkali metal aluminate in solution with an alkali metal hydroxide in contact with a silica source such as sodium silicate, reactive amorphous silica gel, or aqueous colloidal silica sol, at a temperature of about 180° to 200° F. Crystallization occurs over a relatively short period of time, for example, eight to twelve hours, and conversion to the hydrogen form is effected by acid-treating.

Synthetic mordenite prepared in accordance with the above described procedure is available commercially from the Norton Company under the tradename of Zeolon. As with the other zeolites for use in the invention, the hydrogen form of the zeolite is preferred over other forms. Also, it is most highly preferred that the mordenite employed in the invention be a large pore mordenite, i.e., kinetic diameter of the pores is above about 6.0 angstroms.

Another preferred form of crystalline aluminosilicate zeolite for use herein are the zeolites of the ZSM-5 type, such as ZSM-5, ZSM-11, ZSM-12, ZSM-23, ZSM-35, ZSM-38, and the like, with ZSM-5 being most preferred. ZSM-5 is a known zeolite and is more fully described in U.S. Pat. No. 3,702,886 herein incorporated by reference in its entirety; ZSM-11 is a known zeolite and is more fully described in U.S. Pat. No. 3,709,979, herein incorporated by reference in its entirety; ZSM-12 is a known zeolite and is more fully described in U.S. Pat. No. 3,832,449, herein incorporated by reference in its entirety; ZSM-23 is a known zeolite and is more fully described in U.S. Pat. No. 4,076,842, herein incorporated by reference in its entirety; ZSM-35 is a known zeolite and is more fully described in U.S. Pat. No. 4,016,245, herein incorporated by reference in its entirety; and ZSM-38 is a known zeolite and is more fully described in U.S. Pat. No. 4,046,859, herein incorporated by reference in its entirety. These zeolites are known to readily adsorb benzene and normal paraffins, such as n-hexane, and also certain mono-branched paraffins, such as isopentane, but to have difficulty adsorbing di-branched paraffins, such as 2,2-dimethylbutane, and polyalkylaromatics, such as meta-xylene. These zeolites are also known to have a crystal density not less than 1.6 grams per cubic centimeter, a silica-to-alumina ratio of at least 12, and a constraint index, as defined in U.S. Pat. No. 4,229,282, incorporated by reference herein in its entirety, within the range of 1 to 12. The foregoing zeolites are also known to have an effective pore diameter greater than 5 angstroms and to have pores defined by 10-membered rings of oxygen atoms, as explained in U.S. Pat. No. 4,247,388 herein incorporated by reference in its entirety. Such zeolites are preferably utilized in the acid form, as by replacing at least some of the cations contained in the ion exchange sites of the zeolite with hydrogen ions. This exchange may be accomplished directly with an acid or indirectly by ion exchange with ammonium ions followed by calcination to convert the ammonium ions to hydrogen ions. In either case, it is preferred that the exchange be such that a substantial proportion of the ion exchange sites utilized in the catalyst support be occupied with hydrogen ions.

Also suitable for use in the present invention, in place of the zeolite, or in addition thereto, is a microporous crystalline silica. The preferred form of microporous crystalline silica is silicalite, which is disclosed in fuller detail in U.S. Pat. No. 4,061,724, herein incorporated by reference in its entirety. Another microporous crystalline silica suitable for use is silicalite-2, described in "Silicalite-2, A Silica Analogue of the Aluminosilicate Zeolite ZSM-11," by D. M. Bibby et al., *Nature*, Vol. 280, pp. 64 and 65, Aug. 23, 1979. Methods by which silicalite and other microporous crystalline silicas can be used in vanadium and phosphorus-containing catalysts for producing maleic anhydride are disclosed more fully in our U.S. patent application Ser. No. 595,333 filed Mar. 30, 1984, which is herein incorporated by reference in its entirety, and also in our U.S. Pat. No. 4,455,388 herein incorporated by reference in its entirety.

The zeolite and/or microporous crystalline silica in the catalyst of the invention provides a high surface area upon which the vanadium, tin, and phosphorus components are deposited. The crystalline zeolite or microporous crystalline silica also provides physical strength and stability to the catalyst.

To combine the crystalline zeolite and/or crystalline silica with the vanadium, tin, and phosphorus components, the catalyst precursor previously described may be mixed with the crystalline zeolite and/or crystalline silica in a proportion such that 50 to 85 percent of the catalyst comprises the crystalline component, and the balance is the catalyst precursor. Optionally and preferably, however, binding agents and additives are added to provide the proper consistency and strength to the final catalyst. The binding agents and additives, when used, usually comprise from 0.1 to 20, more typically from 0.1 to 10, and preferably from 3 to 10 weight percent, of the finished catalyst. Suitable binding agents include methyl cellulose, silica, and Catapal TM alumina. Additives suitable for use herein include organic polar solvents such as ethanol, propanol, isopropanol, butanol, etc. The preferred method of mixing the catalyst precursor and zeolite is by comulling. However, other mixing techniques may be used.

The physical form of the catalyst of this invention is not critical. The catalyst may be produced as spheres, pellets, beads, elongated cylinders, and three-lobe or clover-leaf configurations. For example, the composites may be filtered and oven-dried and coarse granules may be obtained by breaking up and sieving the oven-dried cake up to any desired size. Spray-drying the catalyst such that the dried catalyst will pass through a 4 to 200 mesh sieve (U.S.) is another method of producing the desired catalyst. Another method involves extruding the catalyst into a desired configuration using a die to produce the desired shape and thereafter drying the catalyst. A particularly desirable shape is a cylindrical configuration having a diameter of from 1/16 inch to ⅛ inch and a length of from ¼ inch to ½ inch.

The final catalyst is activated by calcination which preferably is performed in an air or oxygen atmosphere at a temperature of from about 400° F. to about 1200° F., for about ¼ hour to about 6 hours, usually from about ½ hour to about 4 hours.

The catalyst thus produced is especially suited for converting $C_4$ to $C_8$ mono-olefins to the corresponding diolefin; it usually has a surface area of from 30 $M^2/g$ to 450 $M^2/g$, preferably above 50 $M^2/g$, more preferably from 100 $M^2/g$ to 450 $M^2/g$, a pore volume of from 0.1 cc/g to 0.8 cc/g and a usual compacted bulk density of from 0.35 to 1.50 cc/g, more typically from 0.5 to 1.5 cc/g. A highly preferred surface area for the catalyst of the invention is from 150 to 400 $M^2/g$.

The above-described catalysts of the present invention are useful for oxidative-dehydrogenation reactions, that is, a reaction involving an organic reactant which is converted to a more unsaturated component with the accompanying production of water. Thus, the degree of unsaturation of the product hydrocarbon will be increased in comparison to the feed, and this may be measured by reference to the index of hydrogen deficiency, described by J. B. Hendrickson, D. J. Cram and G. S. Hammond, *Organic Chemistry*, Third Edition, McGraw-Hill, Inc., 1970, at pages 72 and 73 and 82 and 83. This index is described as the number of pairs of hydrogen atoms that must be removed from a saturated alkane to give the empirical formula of a subject compound. For a hydrocarbon, then, the index represents the total of the rings and multiple bonds in a molecule. For compounds containing heteroatoms, the following principles can be used to make the index application: (1) oxygen and sulfur atoms do not change the index; (2) each halogen atom is equivalent to one-half of a hydrogen atom pair; and (3) each nitrogen atom requires that the "reference" saturated alkane be considered as having one extra hydrogen atom (i.e., a formula of $C_nH_{2n+3}$). Thus, it will be seen that the oxidative dehydrogenation reactions herein contemplated, to result in a more unsaturated product, the product must have a hydrogen deficiency at least 1 greater than the reactant.

A variety of reactors may be used to carry out the desired oxidative-dehydrogenation reaction. For example, conventional fluidized bed reactor and fixed-bed or tube, heat exchanger type reactors are satisfactory, the details of the operation of such reactors being well known to those skilled in the art. The oxidation reaction is an exothermic reaction, thus necessitating relatively close control of the reaction temperature. It is desirable to have the surface of the reactor at a constant temperature and some medium may be necessary to conduct heat away from the reactor to aid temperature control. Examples of desirable media include water coolant, molten sulfur, mercury, molten lead, or eutectic salt baths, for example a sodium nitrate-sodium nitrite-potassium nitrate eutectic constant temperature mixture. An additional method of temperature control is to use a metal block reactor whereby the metal surrounding the reactor chamber acts as a temperature regulating body or by conventional heat exchangers.

Normally, a reaction mixture of a gaseous feed stream comprising a molecular oxygen containing gas, for example, air, a mixture of air and oxygen, mixtures of carbon dioxide and oxygen or mixtures of nitrogen or steam with air or oxygen, and a $C_4$ to $C_8$ mono-olefin is charged to the reactor vessel. The gaseous feed stream generally contains a molecular oxygen containing gas and from about 0.1 to 5.0 mole percent, preferably 0.1 to about 3.0 mole percent, more preferably 0.1 to about 2.5 mole percent, and more preferably still, from about 0.1 to about 1.5 mole percent, of a $C_4$ to $C_8$ mono-olefin for optimum yield of the desired diolefin. Although higher concentrations of hydrocarbon may be employed, they are not recommended because explosive hazards may be encountered.

It should be noted that the inert gases, such as helium, may be employed as a diluent or carrier gas in the process herein without deleterious effect upon the dehydrogenation reaction. Nitrogen is the preferred inert gas diluent or carrier.

Olefins which may be used to produce diolefins are preferably selected from mono-olefins containing 4 to 8 carbon atoms. For example, desirable olefins include butene, pentene, cyclopentene, hexene, cyclohexene, heptene, cycloheptene, octene, or a mixture thereof.

In a preferred embodiment, the molecular oxygen and a $C_4$ to $C_8$ mono-olefin are reacted to produce a conjugated diene in the presence of an oxidative-dehydrogenation catalyst of the invention in a pressure reactor. The flow rate of the gaseous feed stream through the pressure reactor may be varied within rather wide limits but a preferred flow rate is such that the gas hourly space velocity (GHSV) is from 2,400 to 6,000 reciprocal hours.

The temperature of reaction may be varied, but normally the reaction should be conducted at temperatures within a rather narrow range. The preferred temperature range for the conversion of $C_4$ to $C_8$ mono-olefins to the corresponding diolefins preferably is from 500° F. to 760° F., and more preferably still, from 600° F. to 700° F.

Typically, the reaction pressure is from atmospheric pressure to 200 p.s.i.g., preferably from atmospheric pressure to 50 p.s.i.g. As previously stated, the reaction may be carried out in any reactor suitable for effecting vapor-phase oxidation reactions, but preferably a fixed catalyst bed reactor is employed.

The preferred product hydrocarbons, as indicated above, are conjugated dienes; however, in alternative embodiments of the invention, the production of other compounds, such as isolated dienes, is contemplated.

The invention is further illustrated by the following examples which are illustrative of various aspects of the invention and are not intended as limiting the scope of the invention as defined by the appended claims.

EXAMPLE I

An oxidative dehydrogenation catalyst having an average oxidation state of 4.72 for vanadium is prepared by charging 14.0 grams (0.12 mole) of ammonium metavanadate, 1.8 grams (0.008 mole) of stannous chloride, 50 ml of distilled water, 10 ml of ethanol, and 11 ml of concentrated hydrochloric acid to an 800-ml round-bottom flask equipped with a water-cooled condenser, heating mantle, and magnetic stirrer. The above-described mixture turns green. Next, 18.0 grams (0 153 mole) of potassium metaphosphate, 15 ml of distilled water, and 16.5 grams (0.198 mole) of 85 percent phosphoric acid are introduced into the flask. This mixture is heated to a temperature of 122° F. and agitated with a magnetic stirrer for 18 hours.

The nonhomogeneous mixture is mixed with 8.0 grams of silica and 120 grams of H+ mordenite using a Model No. 472 Lancaster Mixer, manufactured by Posey Iron Works, Inc., of Lancaster, Pennsylvania. The mixer is operated at 36 RPM. The resulting slurry is air-dried at 230° F. for 12 hours and then calcined in air at 930° F. for two hours. The resulting catalyst is screened to give an 80 to 100 mesh (U.S.) catalyst particle size. The catalyst has a surface area of 41 $M^2$/g and contains a potassium, vanadium, and tin in respective atomic ratios to phosphorus of 0.44 to 1, 0.34 to 1, and 0.23 to 1.

EXAMPLE II

An oxidative dehydrogenation catalyst having an average oxidation state of 4.62 for vanadium and a surface area of 226 $M^2$/gram is prepared by charging 14.0 grams (0.12 mole) of ammonium metavanadate, 1.8 grams (0.008 mole) of stannous chloride, 50 ml of distilled water, 10 ml of ethanol, and 11 ml of concentrated hydrochloric acid to an 800 ml round-bottom flask equipped with a water-cooled condenser, heating mantle, and magnetic stirrer. Then 18 grams (0.152 mole) of potassium metaphosphate, 15 ml of distilled water, and 16.5 grams (0.168 mole) of 85-percent phosphoric acid are introduced into the flask. The mixture is heated to a temperature of 122° F. and agitated with a magnetic stirrer for 12 hours.

The dark green slurry produced above is comulled with 8.0 grams of silica and 120 grams of H+ mordenite using a Model No. 472 Lancaster Mixer, manufactured by Posey Iron Works, Inc., of Lancaster, Pennsylvania. The mixer is operated at 36 RPM. The resulting slurry is calcined in air at 930° F. for three hours. The catalyst thus formed contains potassium, vanadium, and tin in respective atomic ratios to phosphorus of 0.47 to 1, 0.31 to 1, and 0.024 to 1.

EXAMPLE III

An oxidation dehydrogenation catalyst having an average oxidation state of 4.74 for vanadium and a surface area of 142 $M^2$/g is prepared in accordance with the procedure used in Example I with the following exceptions:

38.04 grams (0.28 mole) of potassium metaphosphate and 2.70 grams (0.28 mole) of phosphoric acid are utilized. The resulting catalyst contains potassium, vanadium, and tin in respective atomic ratios to phosphorus of 0.91 to 1, 0.39 to 1, and 0.026 to 1.

EXAMPLE IV

An oxidation dehydrogenation catalyst having a surface area of 363 $M^2$/g and an average oxidation state of 4.83 for vanadium is prepared using the procedure described in Example II with the following exceptions:

3.3 grams (0.028 mole) of potassium metaphosphate and 27.4 grams (0.028 mole) of phosphoric acid are used. The catalyst contains potassium, vanadium, and tin in respective atomic ratios to phosphorus of 0.09 to 1, 0.39 to 1, and 0.026 to 1.

EXAMPLE V 1,3-butadiene is produced from butene by charging 1 ml (0.40 gram) of the catalyst of Example II to a continuous-flow catalytic reaction system equipped with programmable gas chromatograph and marketed commercially under the trade name Flow Diagram S Chematic—CDS 800 CF-HP/GC Catalytic Reaction System, by the Chemical Data Systems, Inc., Oxford, Pa. The reactor is a downflow tubular reactor having a length of 9 inches, an outside diameter of ⅜ inch, an inside diameter of ¼ inch. In addition, the reactor is equipped with a 1/16-inch outside diameter, central-longitudinal thermowell. A feed stream comprising 74.5 volume percent helium, 24.5 volume percent oxygen, and 1 volume percent 1-butene is charged to the reactor at a rate of 2.65 standard cubic feet (SCF)/hour. The gas-hourly space velocity (GHSV) is 4,500 reciprocal hours and the catalyst bed temperature is 752° F. at atmospheric pressure. Analysis indicates that 65.30 percent of the butene is converted to 1,3-butadiene, with a selectivity of 91.80 percent and a yield of 59.95 percent.

EXAMPLE VI 1,3-butadiene is produced from butene by charging 1 ml (0.43 gram) of the catalyst of Example III to a continuous-flow catalytic reaction system equipped with programmable gas chromatograph and marketed commercially under the trade name, Flow Diagram-S Chematic—CDS 800 CF-HP/GC Catalytic Reaction System, by the Chemical Data Systems, Inc., Oxford, Pa. The reactor is a downflow tubular reactor having a length of 9 inches, an outside diameter of ⅜ inch, an inside diameter of ¼ inch. In addition, the reactor is equipped with a 1/16-inch outside diameter, central-longitudinal thermowell. A feed stream comprising 74.5 volume percent helium, 24.5 volume percent oxygen, and 1 volume percent 1-butene is charged to the reactor at a rate of 2.65 standard cubic feet (SCF)/hour. The gas-hourly space velocity (GHSV) is 4,500 reciprocal hours and the catalyst bed temperature is 752° F. at atmospheric pressure. Analysis indicates that 60.60 percent of the butene is converted to 1,3-butadiene, with a selectivity of 90.60 percent and a yield of 54.90 percent.

EXAMPLE VII 1,3-butadiene is produced from butene by charging 1 ml (0.39 gram) of the catalyst of Example IV to a continuous-flow catalytic reaction system equipped with programmable gas chromatograph and marketed commercially under the trade name, Flow Diagram-S Chematic—CDS 800 CF-HP/GC Catalytic Reaction System, by the Chemical Data Systems, Inc., Oxford, Pa. The reactor is a downflow tubular reactor having a length of 9 inches, an outside diameter of ⅜ inch, an inside diameter of ¼ inch. In addition, the reactor is equipped with a 1/16-inch outside diameter, central-longitudinal thermowell. A feed stream comprising 74.5 volume percent helium, 24.5 volume percent oxygen, and 1 volume percent 1-butene is charged to the reactor at a rate of 2.65 standard cubic feet (SCF)/hour. The gas-hourly space velocity (GHSV) is 4,500 reciprocal hours and the catalyst bed temperature is 797° F. at atmospheric pressure. Analysis indicates that 69.5 percent of the butene is converted to 1,3-butadiene, with a selectivity of 88.2 percent and a yield of 61.30 percent.

As can readily be determined from the above Examples, the oxidative dehydrogenation zeolitic catalysts herein effectively promote the conversion of mono-olefins, for example, 1-butene, to diolefins, such as 1,3-butadiene, under the described reaction conditions. Although the invention is not to be limited to any particular theory of operation, it is believed that the reason zeolites of low silica-to-alumina ratio (i.e., 6.0 or below) yield poor results with respect to the production of diolefins is that the oxidation activity of the catalyst is adversely affected by a reaction (possibly a complexing) between the phosphorus component and the alumina in low silica-to-alumina zeolites, whether the alumina is present in an octahedral or tetrahedral form. Evidently, high silica-to-alumina ratios offer more protection to the alumina, preventing such reactions from occurring. In the following example, the poor oxidation activity obtained with low silica-to-alumina ratio zeolites is illustrated.

EXAMPLE VIII

An oxidation catalyst is prepared by charging 28.0 grams of ammonium metavanadate and 100 ml of water to a 500-cc round-bottom flask equipped with a water-cooled condenser, heating mantle, and magnetic stirrer. The resultant mixture is heated to a temperature of 130° F. and agitated with the magnetic stirrer for three minutes. Next, 20 ml of concentrated hydrochloric acid, 3.6 grams of stannous chloride, 20 ml of ethyl alcohol and 60.4 grams of 85 percent phosphoric acid are added to the above mixture. The nonhomogeneous solution thus formed exhibits a green color. Finally, the solution is refluxed for 16 hours: however, a shorter reflux time period may be used, for example, $\frac{1}{2}$ hour or more.

One hundred fifty milliliters of the dark green slurry produced by refluxing is mixed with 240 grams of hydrothermally stabilized Y zeolite having a silica-to-alumina ratio of 5.4. (The zeolite was prepared according to methods disclosed in U.S. Pat. Nos. 3,929,672 and 4,036,739.) The resultant slurry is comulled with 20 grams of amorphous silica and 4 grams of methyl cellulose to achieve the proper consistency, using a Model No. 472 Lancaster Mixer, manufactured commercially by the Posey Iron Works, Inc. Lancaster, Pa. The mixer is operated at a speed of 36 RPM. The resulting slurry is extruded into cylindrical extrudates having an average length of $\frac{1}{8}$ inch and an average diameter of 1/16 inch. The catalyst is activated by calcination at 932° F. in air for 3 hours and has a vanadium-phosphorus-tin atomic ratio of 0.43:1:0.034. The resulting catalyst had an average oxidation state of greater than +4.95 and, when tested for the oxidation of butene and butane to maleic anhydride, was found to exhibit essentially no activity for the desired conversion.

(It will be noted, in this Example VIII, that the catalyst described is not an oxidative-dehydrogenation catalyst of the invention but is rather a hydrocarbon oxidation catalyst for producing maleic anhydride. But the deactivation of the zeolite in the catalyst is indicative of what would occur with oxidative-dehydrogenation catalysts having a similar zeolite.)

EXAMPLE IX

An oxidative dehydrogenation catalyst having an average oxidation state of 4.46 for vanadium is prepared by charging 14.0 grams (0.12 moles) of ammonium metavanadate, 1.8 grams (0.008 moles) of stannous chloride, 50 ml of distilled water, 10 ml of ethanol and 11 ml of concentrated hydrochloric acid to an 800-ml round-bottom flask equipped with a water-cooled condenser, heating mantle and magnetic stirrer. The above-described mixture turns green. Next, 33.04 grams (0.280 moles) of potassium metaphosphate, 15 ml of distilled water and 2.79 grams (0.028 moles) of 85 percent phosphoric acid are introduced into the flask. This mixture is heated to a temperature of 122° F. and agitated with a magnetic stirrer for 18 hours.

The nonhomogeneous mixture is mixed with 8.0 grams of silica, 100 grams of crystalline silica (silicalite), air-dried at 230° F. for 12 hours, and then calcined in air at 932° F. for 3 hours. The resulting catalyst is screened to give an 80 to 200 mesh (U.S.) catalyst particle size. The catalyst has a surface area of 203 $M^2/g$ and a K to P atomic ratio of 0.91:1, V to P atomic ratio of 0.39:1, and a Sn to P atomic ratio of 0.026:1.

EXAMPLE X

An oxidative dehydrogenation catalyst having an average oxidation state of 4.36 for vanadium and a surface area of 247 $M^2$/gram is prepared by charging 14.0 grams (0.120 mole) of ammonium metavanadate, 1.8 grams (0.008 mole) of stannous chloride, 50 ml of distilled water, 10 ml of ethanol and 11 ml of concentrated hydrochloric acid to an 800-ml round-bottom flask equipped with a water-cooled condenser, heating mantle and magnetic stirrer. Then, 18 grams (0.153 mole) of potassium metaphosphate, 15 ml of distilled water and 16.5 grams (0.168 mole) of 85-percent phosphoric acid are introduced into the flask. The mixture is heated to a temperature of 122° F. and agitated with a magnetic stirrer for 12 hours.

The dark green slurry produced above is co-mulled with 8.0 grams of silica and 120 grams of crystalline silica (silicalite) using a Model No. 472 Lancaster Mixer, manufactured by Posey Iron Works, Inc., of Lancaster, Pa. The mixer is operated at 36 RPM. The resulting slurry is calcined in air at 932° F. for 3 hours. The catalyst thus formed has a K to P atomic ratio of 0.48:1, a V to P atomic ratio of 0.37:1, and a Sn to P atomic ratio of 0.025:1.

EXAMPLE XI

An oxidative dehydrogenation catalyst having an average oxidation state of 4.65 for vanadium and a surface area of 276 $M^2/g$ is prepared in accordance with the procedure used in Example X with the following exceptions: 3.30 grams (0.028 mole) of potassium metaphosphate and 27.4 grams (0.280 mole) of phosphoric acid are utilized. The resulting catalyst has a K to P atomic ratio of 0.91:1, a V to P atomic ratio of 0.39:1, and a Sn to P atomic ratio of 0.026:1.

EXAMPLES XII TO XIV 1,3-butadiene is produced from butene by charging 1 cc (0.53 gram) of the catalyst of Example IX to a continuous-flow catalytic reactor system equipped with programmable gas chromatograph and marketed commercially under the trade name Flow Diagram S Chematic-CDS 800 CF-HP/GC Catalytic Reaction System, by the Chemical Data Systems, Inc., Oxford, Pa. The reactor is a downflow tubular reactor having a length of 9 inches, an outside diameter of $\frac{3}{8}$ inch, an inside diameter of $\frac{1}{4}$ inch. In addition, the reactor is equipped with a 1/16- inch outside diameter, central-longitudinal thermowell. A feed stream comprising 74.5 volume percent helium, 24.5 volume percent oxygen, and 0.53 volume percent 1-butene is charged to the reactor at a rate of 0.16 standard cubic feet (SCF) per hour. The gas hourly space velocity (GHSV) is 4,500 reciprocal hours at atmospheric pressure and the catalyst bed temperature is as indicated in Table I below. In addition, the selectivity and yield in Table I are reported as mole percent.

TABLE I

| Example | Temperature (°F.) | Butene Conversion (%) | Butadiene Selectivity (%) | Yield (%) |
|---|---|---|---|---|
| XII | 660 | 70 | 75 | 52.50 |
| XIII | 665 | 60 | 75 | 45.00 |
| XIV | 670 | 65 | 81 | 52.65 |

The above data indicate that the oxidative dehydrogenation catalysts herein are highly selective in producing di-olefins from mono-olefins.

EXAMPLE XV

Butene is selectively oxidized to 1,3-butadiene by charging 1 cc (0.53 gram) of the catalyst of Example X to a continuous-flow catalytic reaction system equipped with programmable gas chromatograph and marketed commercially under the trade name of Flow Diagram S Chematic-CDS 800 CF-HP/GC Catalytic Reaction System, by the Chemical Data Systems, Inc., Oxford, Pa. The reactor is a downflow tubular reactor having a length of 9 inches, an outside diameter of ⅜ inch, and an inside diameter of ¼ inch. In addition, the reactor is equipped with a 1/16-inch outside diameter, central-longitudinal thermowell. A feed stream comprising 74.5 volume percent helium, 24.5 volume percent oxygen, and 0.53 volume percent 1-butene is charged to the reactor at a rate of 0.16 standard cubic feet (SCF) per hour. The gas hourly space velocity (GHSV) is 4,500 reciprocal hours at atmospheric pressure and the temperature is 670° F. Analysis indicates that 75.70 percent of the butene is converted to 1,3-butadiene, with a selectivity of 70 mole percent and a yield of 52.99 mole percent.

Obviously, many modifications and variations of this invention, as hereinbefore set forth, may be made without departing from the spirit and scope thereof. For example, although one embodiment as described above employs a hydrogen zeolite, it is also within the scope of the present invention to introduce the required alkali metal into the zeolite by a cation exchange, as for example, a cation exchange which replaces only a portion of the hydrogen ions in the zeolite with the desired alkali metals. Thus, where the described embodiment would introduce only as much alkali metal into the zeolite as occurs when the zeolite and catalyst precursor are admixed, in alternative embodiments of the invention the zeolite may be deliberately exchanged so as to contain one or more alkali metals. In similar manner, one can introduce some or all of the vanadium required in the present invention into the zeolite. Accordingly, the present invention includes these and other such modifications as fall within the scope of the following claims:

We claim:

1. An oxidative dehydrogenation catalyst comprising components of vanadium, phosphorus, and an alkali metal in combination with a microporous crystalline silica or a crystalline zeolite having a silica-to-alumina ratio of at least 6.0.

2. An oxidative dehydrogenation catalyst as defined in claim 1 wherein said catalyst contains a crystalline aluminosilicate zeolite.

3. An oxidative dehydrogenation catalyst as defined in claim 1 wherein said catalyst contains a crystalline aluminosilicate zeolite of silica-to-alumina ratio of at least 10.0.

4. A method of preparing an oxidative dehydrogenation catalyst which comprises:
   (A) contacting a vanadium compound and a phosphorus compound and an alkali metal compound with an acidic, aqueous medium and a divalent tin compound under reaction conditions which provide vanadium having an average valence of from +3.50 to +4.95 to form a catalyst precursor;
   (B) mixing the catalyst precursor with a carrier material; and
   (C) calcining the resultant mixture at an elevated temperature.

5. A method as defined in claim 4 wherein said carrier material contains a microporous crystalline silica or a crystalline aluminosilicate zeolite having a silica-to-alumina ratio of at least 6.0.

6. A method as defined in claim 5 wherein said catalyst contains a crystalline aluminosilicate zeolite of silica-to-alumina ratio of at least 10.0, and said medium contains an alcohol.

7. A catalyst as defined in claim 1 wherein said catalyst contains a crystalline aluminosilicate zeolite of silica-to-alumina ratio of at least 12.0

8. A catalyst as defined in claim 1 wherein said catalyst contains a crystalline aluminosilicate zeolite of silica-to-alumina ratio of at least 20.0.

9. A catalyst as defined in claim 1 wherein said catalyst contains a crystalline aluminosilicate zeolite of silica-to-alumina ratio no greater than about 150 to 1.

10. A catalyst as defined in claim 1 further comprising a tin component.

11. A catalyst as defined in claim 2 further comprising a tin component.

12. A catalyst as defined in claim 3 further comprising a tin component.

13. A catalyst as defined in claim 7 further comprising a tin component.

14. A catalyst as defined in claim 9 further comprising a tin component.

15. An oxidative-dehydrogenation catalyst comprising components of vanadium, phosphorus, and one or more alkali metals, with the atomic ratio of total alkali metals to phosphorus being above about 0.4:1.0.

16. A catalyst as defined in claim 15 wherein said atomic ratio is no greater than about 1:1.

17. A catalyst as defined in claim 16 further containing tin.

* * * * *